United States Patent [19]

Obayashi et al.

[11] Patent Number: 4,886,656
[45] Date of Patent: Dec. 12, 1989

[54] AGRICULTURAL COMPOSITION WITH REDUCED TOXICITY TO FISHES AND SHELLFISHES

[75] Inventors: Hisashi Obayashi, Gamou; Chikara Tanabayashi, Suita; Akiyoshi Asaka, Kyoto; Yukio Gotou, Suita, all of Japan

[73] Assignee: Takeda Chemical Industries, Ltd., Osaka, Japan

[21] Appl. No.: 124,391

[22] Filed: Nov. 20, 1987

Related U.S. Application Data

[63] Continuation of Ser. No. 821,179, Jan. 22, 1986, abandoned.

[30] Foreign Application Priority Data

Jan. 24, 1985 [WO] PCT Int'l Appl. ... PCT/JP85/00027

[51] Int. Cl.$^4$ .................. A01N 43/08; A01N 57/10
[52] U.S. Cl. ................................. 424/10; 514/147; 514/469; 514/974
[58] Field of Search .................. 514/974, 147, 469; 424/10

[56] References Cited

U.S. PATENT DOCUMENTS 4,288,451 9/1981 Mues et al. .................. 514/147
4,342,778 2/1982 Drabek et al. .................. 424/285

FOREIGN PATENT DOCUMENTS 50-6725 1/1975 Japan .
56-169601 12/1981 Japan .
59-167507 9/1984 Japan .

OTHER PUBLICATIONS

Drabeh et al., C.A. vol. 90 (1979), 90:23028n.

Primary Examiner—Allen J. Robinson
Attorney, Agent, or Firm—Edward McC. Roberts

[57] ABSTRACT

Agricultural formulation with reduced toxicity to fishes and shellfishes, characterized by comprising a lipophilic agriculturally active ingredient (I) and an organic compound (II) having a partition coefficient to the said compound (I) in water of no less than $10^2$ and a process for the production of the said formulation.

10 Claims, No Drawings

AGRICULTURAL COMPOSITION WITH REDUCED TOXICITY TO FISHES AND SHELLFISHES

This application is a continuation of application Ser. No. 821,179, filed Jan. 22, 1986, now abandoned.

The present invention relates to an agricultural composition which remarkably reduces toxicity of lipophilic agriculturally active constituents to fishes and shellfishes and a process for the production thereof.

Recently great many compounds having agricultural activities such as insecticidal, bactericidal and herbicidal activities have been developed and many of them have excellent activities. Most of them have been, however, applied only to fruit trees and vegetables, but not to paddy fields due to their strong toxicity to fishes and shellfishes. Therefore, a great effort has been made to overcome the drawback that these agricultural compounds can not be applied to the paddy field. There has been suggested the following two methods to reduce the toxicity to fishes and shellfishes; (1) a method to reduce the elution of agriculturally active substance to water and (2) a method to add an agent to reduce the toxicity. As to (2), a method to reduce the toxicity of thiocarbamate herbicides (Japanese published unexamined patent application Sho 59-167507) is the only method so far known. Thus, there has been known no fish-toxicity reducing agent applicable to all agricultural compounds. As to (1), since the maintenance of the effect is expected, there has been made quite a number of studies. So far, a composition comprising by compounding an active ingredient with active carbon and vegetable oil (Japanese published unexamined patent application Sho 56-169601), a composition comprising by mixing a petroleum type resin and surfactant with an active ingredient (Japanese published unexamined patent application Sho 50-6725) and a composition comprising by adsorbing an active ingredient into a granular material with dents have been known. They have, however, not stable effect nor enough effect.

The inventors of the present invention have diligently carried out studies on the method to reduce the toxicity to fishes and shellfishes which can be generically applied to a broad scope of lipophilic agriculturally active ingredients. As a consequence, the inventors have found that the toxicity to fishes and shellfishes can be remarkably reduced by adding a certain organic compound to the lipophilic agriculturally active substance and accomplished the present invention by further study.

The present invention relates to an agricultural composition with reduced toxicity to fishes and shellfishes, characterized by containing a lipophilic agriculturally active constituent (I) and an organic compound (II) of which partition coefficient to the said active constituent (I) in water is not less than $10^2$.

The lipophilic agriculturally active constituent means, in the present invention, compounds having insecticidal, bactericidal, herbicidal etc activities and having lipophilic property. The lipophilic property means water-sparingly soluble or water-insoluble in the present invention. The technology of the present invention is applicable whenever the said compounds show toxicity to fishes and shellfishes and the reduction of toxicity is required. The following can be mentioned as the constituents (I); i.e. carbofuran type insecticides, pyrethroid type insecticides, carbamate type insecticides, lipophilic organic phosphorus type insecticides etc. as lipopholic insecticides, CAPTAN [N-(trichloromethylthio)-4-cyclohexene-1,2-dicarboximide, Chevron Chemical Co.], CAPTAFOL [N-(1,1,2,2-tetrachloroethylthio)-4-cyclohexene-1,2-dicarboximide, Chevron Chemical Co.], ANILAZINE [2,4-dichloro-6-(o-chloroanilino)-1,3,5-triazine, Chemagro Agricultural Chemicals Div.], TPN [DACONIL, tetrachloroisophthalonitrile, Diamond Alkali Co.] etc. as lipophilic bactericides, IOXYNIL [4-cyano-2,6-diiodophenyl octanoate, May & Baker, Ltd.], DNBP [2-sec-butyl-4,6-dinitrophenol, Farbwerke Hoechst AG], NAPROANILIDE [2-(β-naphthyloxy)propionamide, Mitsui Toatsu Chemicals, Inc.], PIPEROPHOS [S-(2-methylpiperidinocarbonylmethyl) dipropyl phospholothiolothionate, Ciba-Geigy] etc. as lipophilic herbicides etc. Among those mentioned, Carbofuran type insecticides, pyrethroid type insecticides etc. are particularly often used.

As the carbofuran type insecticides, FURATHIOCARB [butyl 2,3-dihydro-2,2-dimethylbenzofuran-7-yl N,N'-dimethyl-N,N'-thiodicarbamate, Ciba-Geigy], CARBOFURAN [2,3-dihydro-2,2-dimethylbenzofuran-7-yl N-methylcarbamate, FMC Corp., Bayer AG.], CARBOSULFAN [ADVANTAGE, 2,3-dihydro-2,2-dimethylbenzofuran-7-yl N-(dibutylaminothio)-N-methylcarbamate, FMC Corp.], AMINOSULFURAN [ONCOL, AMINOFRACARB, ethyl N-[N'-(2,3-dihydro-2,2-dimethylbenzofuran-7-yloxycarbonyl)-N'-methylaminothio]-N-isopropyl β-alaninate, Otsuka Pharmaceutical Co., Ltd.] are exemplified. As the pyrethroid type insecticides, ALLETHRIN (±)-3-allyl-2-methyl-4-oxo-2-cyclopentenyl (±)-cis, trans-chrysanthemate, Sumitomo Chemical Co., Ltd.], MEOTHRIN [FENPROPATHRIN, (RS)-α-cyano-3-phenoxybenzyl 2,2,3,3-tetramethylcyclopropanecarboxylate, Sumitomo Chemical Co., Ltd.], FLUCYTHRINATE [PAY-OFF, (RS)-α-cyano-3-phenoxybenzyl (S)-2-(4-difluoromethoxyphenyl)-3-methylbutyrate, American Cyanamid Co.], ETHOFENPROX [Trebon, 2-(4-ethoxyphenyl)-2-methylpropyl 3-phenoxybenzyl ether, Mitsui Toatsu Chemicals, Inc.], CHRYSRON-FORTE [d-resmethrin, 5-benzyl-3-furylmethyl (1RS,3RS; 1RS,3SR)-2,2-dimethyl-3-(2-methylpropen-1-yl)cyclopropanecarboxylate, Sumitomo Chemical Co., Ltd.], and natural pyrethrin [pyrethrin I+pyrethrin II] are exemplified. As the carbamate type insecticides, BPMC [o-sec-butylphenyl N-methylcarbamate, Kumiai Chemical Industry], MIPC [o-cumenyl N-methylcarbamate, Mitsubishi Chemical Industries, Ltd.], NAC [CARBARYL, 1-naphthyl N-methylcarbamate, Union Carbide Corp.], CARTAP [S,S'-[2-(dimethylamino)trimethylene] bis(thiocarbamate), Takeda Chemical Industries, Ltd.], and RUBAN [S,S'-[2-(dimethylamino)trimethylene]bis(benzenethiosulfonate), Takeda Chemical Industries, Ltd.] are exemplified. As the lipophilic phosphorus type insecticides, SUMITHION [MEP, dimethyl 4-nitro-m-tolyl phosphorothionate, Sumitomo Chemical Ltd.], MALATHON [S-1,2-bis(ethoxycarbonyl)ethyl dimethyl phosphorothiolothionate, American Cyanamid Co.], ELSAN [PAP, S-[α-(ethoxycarbonyl)benzyl]dimethyl phosphorothiolothionate, Montecatini Edison], PYRACLOFOS [O-[1-(4-chlorophenyl)-4-pyrazolyl] O-ethyl S-propyl phosphorothionate, Takeda Chemical Industries, Ltd.], and DIAZINON [diethyl 2-isopropyl-4-methyl-6-pyrimidinyl phosphorothionate, Ciba-Geigy] are exemplified.

The organic compound (II), another indispensable element of the present invention, are those having the partition coefficient to the said active ingredient (I) in water of no less than $10^2$. Compounds (II) having usually no agricultural activity, but having a high boiling point are used. The compound which is liquid at ordinary temperature (unless explicitly mentioned, the ordinary temperature means 15° C. hereunder) is preferred. In the present invention, the partition coefficient is the partition coefficient ordinarily used as a measure of lipophilic property. It means the constant in the partition law mentioned on page 209 of Encyclopedia Chimica Vol. 8, (edited by Encyclopedia Chimica Editor's Committee, Kyoritsu Shuppan, 1962). Namely, the partition law is defined in the Encyclopedia Chimica as "When a third material (solute) is dissolved in two liquids which are substantially immiscible each other and when they are coexisting, the concentration ratio in these two liquids becomes constant at a fixed temperature regardless of the concentration". The constant value in the partition law is called partition coefficient. The "partition coefficient" in the present invention means also the partition coefficient so defined. In the present invention, the two liquids correspond to the water in paddy fields and organic compound (II), and the solute corresponds to active substance (I). By taking the concentration of active substance (I) to organic compound (II) at ordinary temperature as "Co" and the concentration of active ingredient (I) to water as "Cw", the partition coefficient can be represented by Co/Cw. Namely organic compounds (II) in the present invention mean those sufficing the equation of $Co/Cw \geq 10^2$. Although there is no upper limit of the partition coefficient Co/Cw of organic compound (II) in the present invention, it is preferred to be no more than $10^7$.

Summarizingly, the preferred condition of organic compound (II) is $10^2 \leq Co/Cw \leq 10^7$ (at ordinary temperature). More preferred condition is $10^3 \leq Co/Cw \leq 10^6$ (at ordinary temperature). The ordinary temperature means 15° C. in this case, too.

Among organic compound (II) having the partition coefficient to active ingredient (I) of no less than $10^2$ and preferably no more than $10^7$, the compounds sufficing the following conditions and liquid at ordinary temperature are the most preferred ones:
(i) the solubility to water at ordinary temperature is no more than 5% (by weight)
(ii) boiling point is no lower than 160° C.
(iii) it dissolves no less than 1% (by weight) of active ingredient (I) at ordinary temperature As organic compound (II) sufficing the above mentioned conditions, the followings are exemplified:
(i) fatty acid esters (III) having the following formula $R_1COOR_2$ wherein $R_1$ represents a straight or branched alkyl group of $C_{8-24}$ or an alkenyl group of $C_{8-24}$ and $R_2$ represents a straight or branched alkyl group of $C_{2-12}$
(ii) diesters (IV) having the following formula

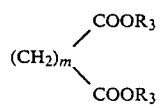

wherein $R_3$ represents a straight or branched alkyl group of $C_{2-12}$ and m represents and integer of 2-4
(iii) phosphates (V) having the following formula

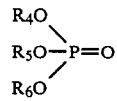

wherein $R_4$, $R_5$, and $R_6$ are same or different and represent a straight or branched alkyl group of $C_{3-12}$, a chlorinated alkyl group of $C_{1-4}$ or a phenyl group
(iv) alkylbenzenes having the following formula (VI)

wherein $R_7$ represents a straight or branched alkyl group of $C_{2-16}$, n means 1-4 showing the number of substituent $R_7$ groups
(v) diphenylmethanes having the following formula (VII)

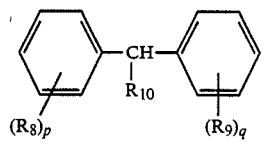

wherein $R_8$, $R_9$, and $R_{10}$ represent a hydrogen atom or a straight or branched alkyl group of $C_{1-3}$, p and q means 1-3 showing the number of substituents $R_8$ and $R_9$ groups
(vi) benzoates (VIII) having the following formula

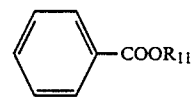

wherein $R_{11}$ represents a straight or branched alkyl group of $C_{1-12}$.
(vii) phthalate (IX) having to following formula

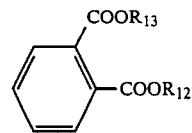

wherein each of $R_{12}$ and $R_{13}$ represents a straight and branched alkyl group of $C_{1-12}$.

As alkyl group ($R_1$) of $C_{8-24}$ in the fatty acid ester (III), $C_{9-19}$ alkyl groups are preferable, e.g. nonyl, undecyl, tridecyl, pentadecyl, heptadecyl are mentioned. As alkenyl group ($R_1$) of $C_{8-24}$ in the same structure, $C_{15-19}$ alkenyl groups are preferable; for instance, oleyl $[C_8H_{17}CH=CH(CH_2)_7-]$, linoleyl $[C_5H_{11}CH=CHCH_2CH=CH(CH_2)_7-]$ etc. are mentioned. In the same way, as $C_{2-12}$ alkyl group ($R_2$), $C_{3-8}$ alkyl groups are preferable; for instance, butyl, amyl, hexyl, heptyl etc. are mentioned. Accordingly, amyl laurate, amyl myristate, butyl palmitate, amyl palmitate, hexyl palmitate, butyl stearate, amyl stearate, hexyl stearate, butyl oleate, amyl oleate, butyl linolate etc. are exemplified as the fatty acid ester (III).

$C_{2-12}$ alkyl groups ($R_3$) of diesters (IV) are preferably $C_{2-10}$ alkyl groups; for instance, ethyl, propyl, butyl, amyl, hexyl, heptyl, octyl, etc. are mentioned. Accordingly, diesters (IV) are illustrated by diethyl succinate, dipropyl succinate, dibutyl succinate, diamyl succinate, dioctyl succinate, diethyl glutamate, dibutyl glutamate, diamyl glutamate, dioctyl glutamate, dibutyl adipate, diamyl adipate, dioctyl adipate etc. as the diester (IV).

$C_{3-12}$ alkyl groups ($R_4$, $R_5$, $R_6$) of phosphate (V) are preferably $C_{4-9}$ alkyl groups; for instance, butyl, amyl, hexyl, octyl etc. In the same structure, $C_{1-4}$ chlorinated alkyl groups ($R_4$, $R_5$, $R_6$) are preferably $C_{2-3}$ chlorinated alkyl groups; for instance, trichloroethyl, trichloropropyl, etc. Accordingly, phosphate esters (V) are for instance, tributyl phosphate, triamyl phosphate, trioctyl phosphate, butyl diphenyl phosphate, octyl diphenyl phosphate, tri(chloroethyl) phosphate etc. as the phosphate (V).

$C_{2-16}$ alkyl groups ($R_7$) of alkylbenzene (VI) are preferably $C_{2-10}$ alkyl groups; for instance, ethyl, propyl, isopropyl, butyl, isobutyl, sec-butyl, tert-butyl, amyl, isoamyl, tert-amyl, octyl, decyl etc. Compounds (VI) are those having 1-4 same or different substituents mentioned above in the benzene ring. Accordingly, alkylbenzene compounds (VI) are exemplified by diethylbenzene, diisopropylbenzene, triisopropylbenzene, tert-butylbenzene, di(tert-butyl)-benzene, diamylbenzene, triamylbenzene, tetraamylbenzene, tert-amylbenzene, di(tert-amyl)benzene, octylbenzene, dodecylbenzene, didodecylbenzene etc. as the alkylbenzene (VI).

$C_{1-3}$ alkyl groups ($R_8$, $R_9$, $R_{10}$) of diphenylmethanes-(VII) are methyl, ethyl, propyl, isopropyl etc. When $R_8$ is $C_{1-3}$ alkyl group and when 2-3 groups are substituting, these $C_{1-3}$ alkyl groups may be same or different. When $R_9$ is $C_{1-3}$ alkyl group and when there exists 2-3 $R_9$s, they may be same or different. Accordingly, diphenylmethane (VII) is exemplified by phenylxylylethane, phenylxylylpropane, trixylylethane, dixylylmethane, diisoxylylethane etc. as the diphenylmethane (VII).

$C_{1-12}$ alkyl groups ($R_{11}$) of benzoate (VIII) are preferably $C_{1-8}$ alkyl groups; for instance, methyl, ethyl, butyl, amyl, hexyl, octyl etc. are mentioned. Accordingly benzoate (VIII) is exemplified by methyl benzoate, ethyl benzoate, butyl benzoate, amyl benzoate, hexyl benzoate, octyl or nonyl benzoate etc. as the benzoate (VIII).

$C_{1-12}$ alkyl groups ($R_{12}$, $R_{13}$) of phthalate (IX) are preferably $C_{1-8}$ alkyl groups; for instance, methyl, ethyl, butyl, amyl, hexyl, octyl etc. are mentioned. Accordingly, phthalate (IX) is examplified by dimethyl phthalate, diethyl phthalate, dibutyl phthalate, dioctyl phthalate etc. as the phthalates (IX).

Organic compound (II) may be used singly or in plural. The agricultural formulation of the present invention can be prepared by mixing agriculturally active substance (I), organic compound (II) and, if necessary, carriers mentioned below by a conventional method or an equivalent thereof. When the amount of organic compound (II) contained in the agricultural formulation is too little, the effect to reduce the toxicity to fishes and shellfishes is not sufficient, and when the amount is too high, it is not practically convenient nor economical. Therefore, 0.1-5 parts by weight, preferably 0.2-3 parts by weight of organic compound (II) is normally added to one part by weight of the agriculturally active substance (I). The formulation so formed can be in the form of solid i.e. powder, dusty granules, granules etc. preferably dusty granules and granules.

The mixing amount of agriculturally active substance (I) to the total formulation can be optionally decided on the basis of the partition coefficient of active substance (I) to water and organic compound (II), the amount applied and the allowable concentration of active ingredient (I) in the paddy field. Ordinarily, 0.01-10 parts of active ingredient (I) to 100 parts of the total formulation is used.

Although it is not apparent how the toxicity of the agriculturally active substance to fishes and shellfishes can be reduced when the present formulation is applied to a paddy field, it is assumed as follows by taking carbofuran type insecticides and pyrethroid type insecticides as examples. Namely, when the agricultural formulation of the present invention is distributed to the paddy field, the above mentioned insecticidal ingredient (I) is divided into the water of the paddy field and organic compound (II) in accordance with the above mentioned partition coefficient. The concentration of the insecticidal ingredient (I) is kept so low that the toxicity to fishes and shellfishes is not problematic. Furthermore, the insecticidal component (I) is absorbed gradually from the roots of plants and accumulated in the roots and stems. When insects intake the insecticidal component by eating the roots and stems so mentioned, a sufficient insecticidal effect can be exerted. On the other hands, the insecticidal component (I) in the water, even it is absorbed by the roots of the plants, is continuously eluted into the water from the portion divided to organic compound (II) in an amount counterbalancing the partition coefficient. Thus, it can maintain, for a long period of time, a concentration which is not problematic toxic-wise, but effective to insects.

The carriers usable in the production of the agricultural formulation of the present invention are exemplified by solid carriers such as diluents, fillers etc. As such carrier, for instance, vegetable dust (e.g. rice bran, soy bean powder, tobacco powder, wheat powder, starch, wood powder, etc.) or mineral powder (e.g. kaolin, bentonite, calcium phosphate, clays such as acid clay, talcs such as talc, agalmatolite etc., silicas such as diatom earth, mica etc) is used. Further, alumina, sulfur powder, active carbon etc. can be used. They are used singly or in combination of no less than two substances in an amount of 5-90%, preferably 10-80% on the basis of weight relative to the whole composition. Also surfactants, solvents etc. used conventionally for the formulation of agricultural composition may be optionally added.

If necessary, non-lipophilic agriculturally active substance may be optionally added. These non-lipophilic active substances are, for example, non-lipophilic natural insecticides, non-lipophilic organic phosphorus insecticides, tricyclazole type bactericides, benzimidazole type bactericides, copper type bactericides, antibiotics, non-lipophilic organic phosphorus type bactericides etc.

The present agricultural formulation is, as mentioned above, a formulation reduced with the toxicity to fishes and shellfishes, which can be prepared readily and cheaply. Since it can adequately exert excellent activity and the toxicity-reducing effect to fishes and shellfishes after having been stored for a long period of time, the value of the formulation in the industry concerned is very high.

The present invention is further explained by the following examples and test examples, but these examples are simple embodiments, which are not intended to limit the present invention.

EXAMPLE 1

To 5 parts of FURATHIOCARB were added 3 parts of amyl oleate, 87 parts of kaolinite clay and 5 parts of polyvinylalcohol (hereinafter called PVA) and mixed homogeneously. To the resultant mixture was further added 14 parts of water and kneaded. Granules were prepared by granulating the mixture in a granulator followed by drying at 80° C.

EXAMPLE 2

To 5 parts of FURATHIOCARB was added 5 parts of tertamyl-benzene and mixed homogeneously. The resultant homogeneous mixture was adsorbed on 90 parts of silica granules by adding the homogeneous mixture to the silica granules under mixing in a mixer to prepare dusty granules.

EXAMPLE 3

To 5 parts of FURATHIOCARB was added 5 parts of octyl diphenyl phosphate and mixed homogeneously. The resultant homogeneous mixture was adsorbed on 90 parts of Raiton granules (manufactured by Raitoston K.K.) by adding the homogeneous mixture to the Raiton granules under mixing in a mixer to prepare granules.

EXAMPLE 4

To 5 parts of FURATHIOCARB were added 1 part of octyl diphenyl phosphate and 0.5 part of diethyl succinate and mixed homogeneously. The resultant homogeneous mixture was adsorbed on 93.5 parts of Raiton granules (manufactured by Raitoston K.K.) by adding the homogeneous mixture to the Raiton granules under mixing in a mixer to prepare dusty granules.

EXAMPLE 5

To 2 parts of FURATHIOCARB was added 5 parts of phenylxylylethane and mixed homogeneously. The resultant homogeneous mixture was adsorbed on 93 parts of Raiton granules by adding the homogeneous mixture to the Raiton granules under mixing in a mixer to prepare dusty granules.

EXAMPLE 6

To 5 parts of FURATHIOCARB was added 5 parts of phenylxylylethane and mixed homogeneously. The resultant homogeneous mixture was adsorbed on 90 parts of Raiton granules by adding the homogeneous mixture to the Raiton granules under mixing in a mixer to prepare granules.

EXAMPLE 7

To 5 parts of FURATHIOCARB were added 85 parts of talc clay and 5 parts of alpha-starch and mixed homogeneously. To the resultant mixture was further added 14 parts of water and kneaded. Granulating the mixture in a granulator followed by drying at 80° C. gave granules. On the resultant granules was adsorbed 5 parts of ethyl benzoate by adding ethyl benzoate to the above granules under mixing in a mixture to prepare granules.

EXAMPLE 8

To 2 parts of FURATHIOCARB was added 5 parts of dioctyl adipate and mixed homogeneously. The resultant homogeneous mixture was adsorbed on 93 parts of Kagalite granules (manufactured by Tango Kensetsu K.K.) by adding the homogeneous mixture to the Kagalite granules under mixing in a mixer to prepare granules.

EXAMPLE 9

To 1.5 parts of CARBOSULFAN were added 5 parts of octyl diphenyl phosphate, 88.5 parts of talc clay and 5 parts of alpha-starch and mixed homogeneously. To the resultant mixture was further added 14 parts of water and kneaded. Granules were prepared by granulating the mixture in a granulator followed by drying at 80° C.

EXAMPLE 10

To 2 parts of CARBOFURAN was added 6 parts of trioctyl phosphate and mixed homogeneously. The resultant homogeneous mixture was adsorbed on 92 parts of Kagalite granules by adding the homogeneous mixture to the Kagalite granules under mixing in a mixer to prepare granules.

EXAMPLE 11

To 5 parts of FURATHIOCARB was added 5 parts of phenylxylylethane and mixed(mixture A) To 5 parts of polyethylene glycol 6000 was added 5 parts of tricyclazole and mixed under warming at 70° C. to form a homogeneous mixture(mixture B). Mixture A is adsorbed on 80 parts of Raiton granules, followed by addition of mixture B under mixing in a mixer to prepare granules

EXAMPLE 12

To 99 parts of talc clay were added 0.5 part of FURATHIOCARB and 0.5 part of hexyl benzoate to prepare dusty granules.

EXAMPLE 13

To 5 parts of FURATHIOCARB were added 5 parts of tricyclazole, 5 parts of phenylxylylethane, 5 parts of alpha-starch and 80 parts of talc clay and mixed homogeneously. To the resultant mixture was further added 14 parts of water and kneaded. Granules were prepared by granulating the mixture in a granulator followed by drying at 80° C.

EXAMPLE 14

To 5 parts of FURATHIOCARB were added 5 parts of 1,2,5,6-tetrahydropyrrolo[3,2,1-ij]quinoline-4-one, 5 parts of octyl diphenyl phosphate, 5 parts of alpha-starch and 80 parts of talc clay and mixed homogeneously. To the resultant mixture was further added 14 parts of water and kneaded. Granules were prepared by granulating the mixture in a granulator followed by drying at 80° C.

Comparison formulations relating to carbofuran type insecticides are shown below and do not belong to the present invention.

Comparison Formulation 1

On 95 parts of Apls (manufactured by Isolite K.K.) was adsorbed 5 parts of FURATHIOCARB by adding the FURATHIOCARB to the Apls under mixing in a mixer to prepare granules.

Comparison Formulation 2

To 5 parts of FURATHIOCARB were added 90 parts of talc clay and 5 parts of PVA and mixed homogeneously. To the resultant mixture was further added 14 parts of water and kneaded. Granules were prepared by granulating the mixture in a granulator followed by drying at 80° C.

Comparison Formulation 3

To 2 parts of FURATHIOCARB were added 5 parts of alpha-starch and 93 parts of talc clay and mixed homogeneously. To the resultant mixture was further added 14 parts of water and kneaded. Granules were prepared by granulating the mixture in a granulator followed by drying at 80° C.

Fish-toxicity text

Samples were weighed and added into 10 liters of tap water at 23°-26° C., so that 5 mg, 10 mg or 25 mg of each of active constituent in the samples was contained in 10 liters of water. The mixture was placed in a porcelain pot (inner diameter of 26 cm, depth of 30 cm), in which 5 black carp fry(body-length of 4.8-5.0 cm, body weight of 2.8-3.0 g) were freed. Fish-mortality and TLm value (medium Tolerance Limit, concentration to kill 50%) were measured by counting the number of dead bodies after 24 hours and 48 hours from the treatment. The test was repeated twice. The results are shown in Table 1.

TLm value was calculated according to the method described on pages 387-392 of "Fishes as experimental animals(Jikken-doubutsu toshiteno Gyorui, edited by Nobuo Egami, Soft Science Co., 1981)".

TABLE 1
FISH-TOXICITY TEST RESULTS

| Time after release of fish Concentration of active ingredient (ppm)* | Fish mortality (%) | | | | | | 50 Percent lethal Concentration (T L m) 48 hours ppm* |
|---|---|---|---|---|---|---|---|
| | 24 hours | | | 48 hours | | | |
| | 0.5 | 1.0 | 2.5 | 0.5 | 1.0 | 2.5 | |
| Example - 1 | 0 | 10 | 10 | 10 | 20 | 20 | 4.8 |
| 2 | 10 | 10 | 20 | 10 | 10 | 30 | 5.5 |
| 3 | 10 | 20 | 20 | 10 | 20 | 20 | 5.8 |
| 4 | 20 | 20 | 20 | 20 | 30 | 30 | 3.4 |
| 5 | 0 | 10 | 20 | 10 | 20 | 20 | 3.7 |
| 6 | 10 | 20 | 30 | 10 | 20 | 30 | 5.6 |
| 7 | 0 | 20 | 20 | 0 | 20 | 20 | 6.7 |
| 8 | 20 | 30 | 30 | 20 | 30 | 30 | 4.3 |
| 9 | 0 | 0 | 10 | 0 | 0 | 10 | 9.2 |
| 10 | 0 | 0 | 0 | 0 | 0 | 10 | 17.8 |
| 11 | 10 | 20 | 20 | 10 | 20 | 20 | 5.8 |
| 12 | 20 | 20 | 30 | 20 | 30 | 30 | 3.7 |
| 13 | 0 | 10 | 20 | 10 | 20 | 20 | 5.3 |
| 14 | 0 | 10 | 20 | 0 | 20 | 20 | 6.2 |
| comparison 1 | 60 | 100 | 100 | 70 | 100 | 100 | 0.4 |
| 2 | 100 | 100 | 100 | 100 | 100 | 100 | 0.3 |
| 3 | 10 | 10 | 100 | 10 | 10 | 100 | 1.8 |

*0.5 ppm means 5 mg of active constituent contained in 10 l of water
1.0 ppm means 10 mg of active constituent contained in 10 l of water
2.5 ppm means 25 mg of active constituent contained in 10 l of water
TLm (ppm) means mg of active constituent contained in 10 l of water

EXAMPLE 15

To 3 parts of FLUCYTHRINATE was added 3 parts of phenylxylylethane and mixed homogeneously. The resultant homogeneous mixture was adsorbed on 94 parts of silica granules by adding the homogeneous mixture to the silica granules under mixing in a mixer to prepare granules.

EXAMPLE 16

To 1.5 parts of FLUCYTHRINATE were added 2 parts of octyl diphenyl phosphate, 91.5 parts of kaolinite clay and parts of PVA and mixed homogeneously. To the resultant mixture was further added 14 parts of water and kneaded. Granules were prepared by granulating the mixture in a granulator followed by drying at 85° C.

EXAMPLE 17

To 5 parts of ETHOFENPROX was added 5 parts of octyl diphenyl phosphate and mixed homogeneously. The resultant homogeneous mixture was adsorbed on 90 parts of Raiton granules by adding the homogeneous mixture to the Raiton granules under mixing in a mixer to prepare granules.

EXAMPLE 18

To 2.5 parts of ETHOFENPROX was added 2 parts of phenylxylylethane and mixed homogeneously. The resultant homogeneous mixture was adsorbed on 95.5 parts of silica granules by adding the homogeneous mixture to the silica granules under mixing in a mixer to prepare granules.

EXAMPLE 19

To 88.5 parts of kaolinite clay were 5 parts of PVA and 13 parts of water and kneaded. Granules were prepared by granulating the mixture in a granulator followed by drying at 90° C. To 2.5 parts of diethyl phthalate was added 4 parts of ETHOFENPROX and mixed. The resultant mixture was added and adsorbed on the above granules to prepare granules.

EXAMPLE 20

To 0.5 parts of ETHOFENPROX were added 1 parts of octyl diphenyl phosphate, 95.5 parts of kaolinite clay and 3 parts of PVA and mixed homogeneously. To the resultant mixture was further added 15 parts of water and kneaded. Granules were prepared by granulating the mixture in a granulator followed by drying at 85° C.

EXAMPLE 21

To 3 parts of CHRYSRON-FORTE was added 6 parts of phenylxylylethane and mixed homogeneously. The resultant homogeneous mixture was adsorbed on 91 parts of silica granules by adding the homogeneous mixture to the silica granules under mixing in a mixer to prepare granules.

EXAMPLE 22

To 3 parts of CHRYSRON-FORTE was added 3 parts of octyl diphenyl phosphate and mixed homogeneously. The resultant homogeneous mixture was adsorbed on 94 parts of silica granules by adding the homogeneous mixture to the silica granules under mixing in a mixer to prepare granules.

EXAMPLE 23

To 20 parts of natural pyrethrin (containing 18% (W/W) of pyrethrin I+pyrethrin II as active constituent, Dainihon Jochugiku Co., Ltd.) was added 5 parts of octyl diphenyl phosphate and mixed homogeneously.

The resultant homogeneous mixture was adsorbed on 75 parts of Raiton granules by adding the homogeneous mixture to the Raiton granules under mixing in a mixer to prepare granules.

EXAMPLE 24

To 10 parts of natural pyrethrin (containing 18% (W/W) of pyrethrin I+pyrethrin II as active constituent, Dainihon Jochugiku Co., Ltd.) was added 5 parts of phenylxylylethane and mixed homogeneously. The resultant homogeneous mixture was adsorbed on 85 parts of Raiton granules by adding the homogeneous mixture to the Raiton granules under mixing in a mixer to prepare granules.

Comparison formulations relating to pyrethroid type insecticides are shown below and do not belong to the present invention.

Comparison Formulation 4

On 97 parts of silica granules was adsorbed 3 parts of FLUCYTHRINATE by adding the FLUCYTHRINATE to the silica granules under mixing in a mixer to prepare granules.

Comparison Formulation 5

On 95 parts of Raiton granules was adsorbed 5 parts of ETHOFENPROX by adding the ETHOFENPROX to the Raiton granules under mixing in a mixer to prepare granules.

Comparison Formulation 6

On 97 parts of silica granules was adsorbed 3 parts of CHRYSRON-FORTE by adding the CHRYSRON-FORTE to the silica granules under mixing in a mixer to prepare granules.

Comparison Formulation 7

On 90 parts of silica granules was adsorbed 10 parts of natural pyrethrin (containing 18% (W/W) of pyrethrin I+pyrethrin II as active constitute, Dainihon Jochugiku Co., Ltd.) by adding the natural pyrethrin to the silica granules under mixing in a mixer to prepare granules.

Fish-toxicity test

The test was carried out by the method as described above. TLm value was measured by counting the number of dead bodies after 24, 48, 72 and 96 hours from the treatment. The results are shown in Table 2.

TABLE 2

| FISH-TOXICITY TEST RESULTS | | | | |
|---|---|---|---|---|
| Time after release of fish | 50 percent lethal concentration (T L m) ppm* | | | |
| | 24 hours | 48 hours | 72 hours | 96 hours |
| Example - 15 | 0.076 | 0.071 | 0.064 | 0.064 |
| 16 | 0.084 | 0.086 | 0.079 | 0.082 |
| 17 | >20 | >20 | >20 | >20 |
| 18 | >20 | >20 | >20 | >20 |
| 19 | >20 | >20 | >20 | >20 |
| 20 | >20 | >20 | >20 | >20 |
| 21 | >2.0 | 1.4 | — | — |
| 22 | >2.0 | 1.7 | — | — |
| 23 | 2.8 | 2.8 | — | — |
| 24 | 1.7 | 1.3 | — | — |
| Comparison - 4 | 0.0013 | 0.0013 | 0.0013 | 0.0013 |
| 5 | 7.1 | 7.1 | 0.56 | 0.21 |
| 6 | 0.7 | 0.7 | — | — |
| 7 | 0.13 | 0.13 | — | — |

*ppm means mg of active constituent contained in 10 l of water
— not tested

EXAMPLE 25

To 3 parts of DIAZINON was added 6 parts of octyl diphenyl phosphate and mixed homogeneously. The resultant homogeneous mixture was adsorbed on 91 parts of Raiton granules by adding the homogeneous mixture to the Raiton granules under mixing in a mixer to prepare granules.

EXAMPLE 26

To 3 parts of DIAZINON was added 6 parts of phenylxylylethane and mixed homogeneously. The resultant homogeneous mixture was adsorbed on 91 parts of Raiton granules by adding the homogeneous mixture to the Raiton granules under mixing in a mixer to prepare granules.

EXAMPLE 27

To 3 parts of MALATHON was added 6 parts of phenylxylylethane and mixed homogeneously. The resultant homogeneous mixture was adsorbed on 91 parts of Raiton granules by adding the homogeneous mixture to the Raiton granules under mixing in a mixer to prepare granules.

EXAMPLE 28

To 3 parts of MALATHON was added 6 parts of octyl diphenyl phosphate and mixed homogeneously. The resultant homogeneous mixture was adsorbed on 91 parts of Raiton granules by adding the homogeneous mixture to the Raiton granules under mixing in a mixer to prepare granules.

EXAMPLE 29

To 2 parts of MALATHON was added 2 parts of dimethyl phthalate and mixed homogeneously. The resultant homogeneous mixture was adsorbed on 96 parts of silica granules by adding the homogeneous mixture to the silica granules under mixing in a mixer to prepare granules.

EXAMPLE 30

To 3 parts of ELSAN was added 6 parts of phenylxylylethane and mixed homogeneously. The resultant homogeneous mixture was adsorbed on 91 parts of Raiton granules by adding the homogeneous mixture to the Raiton granules under mixing in a mixer to prepare granules.

EXAMPLE 31

To 1.5 parts of ELSAN was added 1.5 parts of phenylxylylethane and mixed homogeneously. The resultant homogeneous mixture was adsorbed on 97 parts of Raiton granules by adding the homogeneous mixture to the Raiton granules under mixing in a mixer to prepare granules.

EXAMPLE 32

To 3 parts of SUMITHION was added 6 parts of phenylxylylethane and mixed homogeneously. The resultant homogeneous mixture was adsorbed on 91 parts of Raiton granules by adding the homogeneous mixture to the Raiton granules under mixing in a mixer to prepare granules.

EXAMPLE 33

To 5 parts of SUMITHION was added 5 parts of octyl diphenyl phosphate and mixed homogeneously. The resultant homogeneous mixture was adsorbed on 90 parts of Raiton granules by adding the homogeneous mixture to the Raiton granules under mixing in a mixer to prepare granules.

EXAMPLE 34

To 3 parts of PYRACLOFOS was added 3 parts of dimethyl phthalate and mixed homogeneously. The resultant homogeneous mixture was adsorbed on 94 parts of Raiton granules by adding the homogeneous mixture to the Raiton granules under mixing in a mixer to prepare granules.

EXAMPLE 35

To 3 parts of PYRACLOFOS was added 3 parts of tri(chloroethyl) phosphate and mixed homogeneously. The resultant homogeneous mixture was adsorbed on 94 parts of Raiton granules by adding the homogeneous mixture to the Raiton granules under mixing in a mixer to prepare granules.

Comparison formulations relating to lipophilic organic phosphorus type insecticides are shown below and do not belong to the present invention.

Comparison Formulation 8

On 97 parts of Raiton granules was adsorbed 3 parts of DIAZINON by adding the DIAZINON to the Raiton granules under mixing in a mixer to prepare granules.

Comparison Formulation 9

On 97 parts of Raiton granules was adsorbed 3 parts of MALATHON by adding the MALATHON to the Raiton granules under mixing in a mixer to prepare granules.

Comparison Formulation 10

On 97 parts of Raito granules was adsorbed 3 parts of ELSAN by adding the ELSAN to the Raiton granules under mixing in a mixer to prepare granules.

Comparison Formulation 11

On 97 parts of Raiton granules was adsorbed 3 parts of SUMITHION by adding the SUMITHION to the Raiton granules under mixing in a mixer to prepare granules.

Comparison Formulation 12

On 97 parts of Raiton granules was adsorbed 3 parts of PYRACLOFOS by adding the PYRACLOFOS to the Raiton granules under mixing a mixer to prepare granules.

Fish-toxicity test

The test was carried out by the method as described above. TLm value was measured by counting the number of dead bodies after 24 and 48 hours from the treatment. The results are shown in Table 3.

TABLE 3

| FISH-TOXICITY TEST RESULTS | | |
|---|---|---|
| Time after release of fish | 50 percent lethal concentration (T L m) ppm* | |
| | 24 hours | 48 hours |
| Example - 25 | >16 | 11 |
| 26 | >16 | — |
| 27 | 9.4 | 9.4 |
| 28 | 8.7 | 8.5 |
| 29 | 9.1 | 8.8 |
| 30 | 8.9 | 5.6 |
| 31 | 7.2 | 6.3 |
| 32 | 11 | 11 |
| 33 | 8.7 | 8.1 |
| 34** | — | 0.77 |
| 35** | — | 0.61 |
| Comparison - 8 | 9.0 | 8.7 |
| 9 | 0.89 | 0.87 |
| 10 | 2.8 | 2.8 |
| 11 | 5.6 | 5.6 |
| 12** | — | 0.029 |

*ppm means mg of active constituent contained in 10 l of water
**A grass beaker (inner diameter of 13 cm, depth of 19 cm) in place of the porcelain pot and 5 loaches fry (body length of 9.4 cm, body weight of 5.9 g) in place of 5 black carp fry were used.
— not tested.

EXAMPLE 36

To 3 parts of CARTAP were added 6 parts of phenylxylylethane, 87 parts of kaolinite clay and 4 parts of PVA and mixed homogeneously. To the resultant mixture was further added 16 parts of water and kneaded. Granules were prepared by granulating the mixture in a granulator followed by drying at 85° C.

EXAMPLE 37

To 3 parts of CARTAP were added 9 parts of phenylxylylethane, 84 parts of Kaolinite clay and 4 parts of PVA and mixed homogeneously. To the resultant mixture was further added 15 parts of water and kneaded. Granules were prepared by granulating the mixture in a granulator followed by drying at 85° C.

EXAMPLE 38

To 3 parts of RUBAN were added 6 parts of phenylxylylethane, 87 parts of Kaolinite clay and 4 parts of PVA and mixed homogeneously. To the resultant mixture was further added 15 parts of water and kneaded. Granules were prepared by granulating the mixture in a granulator followed by drying at 70° C.

EXAMPLE 39

To 3 parts of RUBAN were added 6 parts of octyl diphenyl phosphate, 87 parts of Kaolinite clay and 4 parts of PVA and mixed homogeneously. To the resultant mixture was further added 15 parts of water and kneaded. Granules were prepared by granulating the mixture in a granulator followed by drying at 70° C.

Comparison formulations relating to carbamate type insecticides are shown below and do not belong to the present invention.

Comparison Formulation 13

To 3 parts of CARTAP were added 93 parts of Kaolinite clay and 4 parts of PVA and mixed homogeneously. To the resultant mixture was further added 14 parts of water and kneaded. Granules were prepared by granulating the mixture in a granulator followed by drying at 85° C.

Comparison Formulation 14

To 3 parts of RUBAN were added 93 parts of Kaolinite clay and 4 parts of PVA and mixed homogeneously. To the resultant mixture was further added 15 parts of water and kneaded. Granules were prepared by granulating the mixture in a granulator followed by drying at 70° C.

Fish-toxicity test

The test was carried out by the method as described above. TLm value was measured by counting the number of dead bodies after 24 and 48 hours from the treatment. The results are shown in Table 4.

TABLE 4
FISH-TOXICITY TEST RESULTS

| Time after release of fish | | 50 percent lethal concentration (T L m) ppm* | |
|---|---|---|---|
| | | 24 hours | 48 hours |
| Example - | 36 | 1.4 | 1.4 |
| | 37 | 1.7 | 1.5 |
| | 38 | >12 | >12 |
| | 39 | >30 | 13 |
| Comparison - | 13 | 1.2 | 0.79 |
| | 14 | 6.0 | 6.0 |

*ppm means mg of active constituent contained in 10 l of water

EXAMPLE 40

To 3 parts of TPN were added 6 parts of phenylxylylethane, 88 parts of kaolinite clay and 3 parts of PVA and mixed homogeneously. To the resultant mixture was further added 13 parts of water and kneaded. Granules were prepared by granulating the mixture in a granulator followed by drying at 87° C.

EXAMPLE 41

To 3 parts of TPN were added 6 parts of octyl diphenyl phosphate, 88 parts of kaolinite clay and 3 parts of PVA and mixed homogeneously. To the resultant mixture was further added 14 parts of water and kneaded. Granules were prepared by granulating the mixture in a granulator followed by drying at 90° C.

Comparison formulation relating to lipophilic bactericide is shown below and does not belong to the present invention.

Comparison Formulation 15

To 3 parts of TPN were added 93 parts of kaolinite clay and 4 parts of PVA and mixed homogeneously. To the resultant mixture was further added 14 parts of water and kneaded. Granules were prepared by granulating the mixture in a granulator followed by drying at 85° C.

Fish-toxicity test

The test was carried out by the method as described above. TLm vale was measured by counting the number of dead bodies after 24 and 48 hours from the treatment. The results are shown in Table 5.

TABLE 5
FISH-TOXICITY TEST RESULTS

| Time after release of fish | | 50 percent lethal concentration (T L m) ppm* | |
|---|---|---|---|
| | | 24 hours | 48 hours |
| Example - | 40 | >12 | 9.2 |
| | 41 | >12 | >12 |
| Comparison - | 15 | 8.5 | 7.8 |

*ppm means mg of active constituent contained in 10 l of water

What we claim is:

1. An agricultural composition, with reduced toxicity to fish and shellfish, which consists essentially of 0.01 to 10 parts of a lipophilic agriculturally-active constituent relative to 100 parts of the total composition selected from the group consisting of carbofuran and carbamate type insecticides and an organic liquid in which said active constituent has a partition coefficient versus water of not less than $10^2$, said organic liquid being present in an amount which is effective to reduce the toxicity of the agriculturally active constituent to fish and shellfish wherein said organic liquid is a phosphate of the formula:

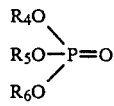

in which each of $R_4$, $R_5$ and $R_6$ are alkyl of 3 to 12 carbon atoms, chlorinated alkyl of 1 to 4 carbon atoms or phenyl.

2. The agricultural composition of claim 1, wherein the lipophilic agriculturally-active constituent is a carbofuran type insecticide.

3. The agricultural composition of claim 2, wherein the carbofuran type insecticide is butyl 2,3-dihydro-2,2-dimetyl-benzofuran-7-yl N,N'-dimethyl-N,N'-thiodicarbamate.

4. The agricultural composition of claim 1, wherein the lipophilic agriculturally-active constituent is a carbamate type insecticide.

5. The agricultural composition of claim 1, wherein the organic liquid is one wherein the partition coefficient of the lipophilic agriculturally-active constituent is in the range of $10^2$ to $10^7$.

6. The agricultural composition of claim 1, wherein the phosphate is octyl diphenyl phosphate or trioctyl phosphate.

7. The agricultural composition of claim 1, wherein the amount of the organic liquid is in the range of 0.1 to 5 parts by weight per one part by weight of the lipophilic agriculturally-active constituent.

8. The agricultural composition of claim 1, which further includes an inert carrier.

9. The agricultural composition of claim 8, wherein the amount of the carrier is in the range of 5 to 90% by weight relative to the whole agricultural composition.

10. A method of benefitting an agricultural area comprising the step of applying thereto an agriculturally beneficial amount of an agricultural composition which consists essentially of (1) 0.01 to 10 parts of a lipophilic agriculturally-active constituent relative to 100 parts of total composition selected from the group consisting of carbofuran and carbamate type insecticides, and (2) an organic liquid in which said active constituent has a partition coefficient versus water of not less than $10^2$, said organic liquid being present in an amount which is effective to reduce the toxicity of the agriculturally active constituent to fish and shellfish wherein said organic liquid is a phosphate of the formula:
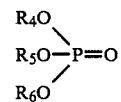
in which each of $R_4$, $R_5$ and $R_6$ are alkyl of 3 of 12 carbon atoms, chlorinated alkyl of 1 to 4 carbon atoms or phenyl.
* * * * *